United States Patent [19]

Shen et al.

[11] 4,094,662

[45] June 13, 1978

[54] MORPHOLINOBENZIMIDAZOLE N-OXIDES

[75] Inventors: Kelvin Kei-Wei Shen, Fountain Valley, Calif.; Wayne Stuart Belles, Moscow, Id.

[73] Assignee: United States Borax & Chemical Corporation, Los Angeles, Calif.

[21] Appl. No.: 776,395

[22] Filed: Mar. 10, 1977

Related U.S. Application Data

[63] Continuation-in-part of Ser. No. 671,452, Mar. 29, 1976, Pat. No. 4,049,422.

[51] Int. Cl.$^2$ .................... A01N 9/22; C07D 498/04
[52] U.S. Cl. ......................................... 71/92; 544/101
[58] Field of Search ............................. 544/101; 71/92

[56] References Cited

PUBLICATIONS

Saunders, *J. Chem. Soc.*, London, pp. 3275–3277 (1955).
Fielden et al., *Tetrahedron Letters.*, pp. 1229–1234 (1970), No. 15.
Nair et al., *J. Am. Chem. Soc.*, vol. 83, pp. 3518–3521 (1961).

*Primary Examiner*—John M. Ford
*Attorney, Agent, or Firm*—James R. Thornton

[57] ABSTRACT

Tricyclic 1,2-morpholinobenzimidazole N-oxides having a trifluoromethyl or branched-chain alkyl group on the aromatic ring para to the morpholino nitrogen. The compounds are herbicidal and can be used as intermediates for preparing herbicidal compounds.

12 Claims, No Drawings

MORPHOLINOBENZIMIDAZOLE N-OXIDES

This application is a continuation-in-part of our copending application Ser. No. 671,452 filed Mar. 29, 1976, now U.S. Pat. No. 4,049,422.

This invention relates to novel tricyclic morpholinobenzimidazole N-oxide compounds which are useful as intermediates for preparing herbicidal compounds and possess herbicidal activity in their own right.

BACKGROUND OF THE INVENTION

Nair and Adams, in the *Journal of the American Chemical Society*, Vol. 33, pp. 3518–3521 (1961), describe the preparation of certain tricyclic morpholinobenzimidazole compounds by the oxidative cyclization of ortho-anilinomorpholine compounds with peroxytrifluoroacetic acid. The reaction can be illustrated by the following equation.

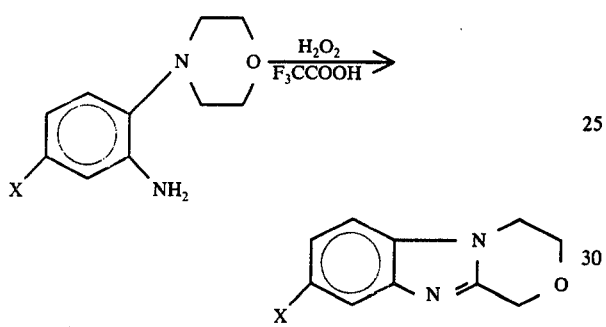

in which X represents hydrogen, chloro, methyl or nitro.

Fielden et al., *Journal of the Chemical Society*, No. 7, pages 696–701 (1973) report the preparation of 1,2-morpholinobenzimidazole N-oxide and its 5-nitro derivative by cyclization of the corresponding ortho-nitrophenylmorpholine compound.

SUMMARY OF THE INVENTION

This invention provides a class of novel morpholinobenzimidazole-N-oxide compounds of the formula

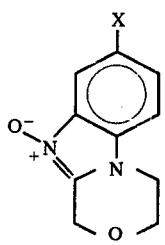

in which X represents a branched-chain alkyl group of three to about six carbon atoms or trifluoromethyl. The compounds may also be named as 5-substituted-1,2-(gamma-oxa-tetramethylene) benzimidazole-N-oxides. Thus, in addition to trifluoromethyl, X can represent branched-chain alkyl groups such as isopropyl, tertiarybutyl, isoamyl, cyclopropyl, secondary-butyl, secondary-pentyl, and the like.

The compounds of this invention are useful as intermediates for the preparation of herbicidal 1,2-morpholinobenzimidazole compounds by a chemical reduction reaction such as with hydrogen over platinum catalyst. The synthesis can be illustrated by the following equation.

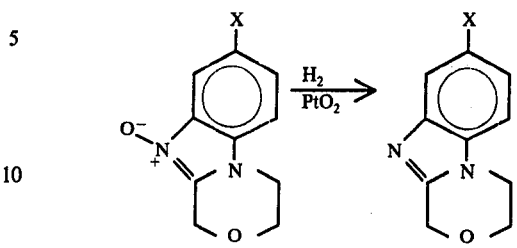

in which X has the significance previously assigned. The compounds are also useful as herbicides, being active as both preemergence and post-emergence treatments.

The compounds of this invention may be prepared by the cyclization of the corresponding ortho-nitrophenylmorpholine compound by use of refluxing hydrochloric acid, according to the following equation.

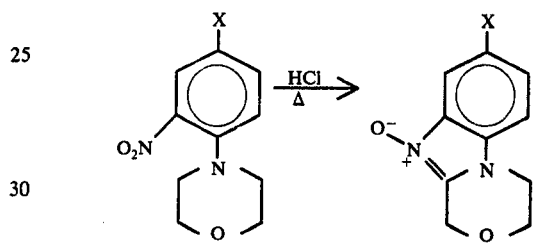

Dilute hydrochloric acid, such as containing about 20% HCl, is merely heated with the nitrophenylmorpholine at reflux temperature in a reaction vessel. The resultant aqueous solution is then neutralized, such as with sodium carbonate, and extracted with an organic solvent such as methylene chloride from which the desired N-oxide product may be isolated.

The nitrophenylmorpholine starting materials are readily prepared by reaction of morpholine with the corresponding 2-nitrochlorobenzene compound.

The following examples illustrate preparation of representative compounds of this invention.

EXAMPLE I 4-(2-Nitro-4-trifluoromethylphenyl)morpholine 4-(2-Nitro-4-trifluoromethylphenyl)morpholine was prepared by reaction of 4-chloro-3-nitrobenzotrifluoride with equimolar amounts of morpholine and triethylamine in monoglyme. The resultant product melts at 37°–39° C.

EXAMPLE 2

5-trifluoromethyl-1,2-(gamma-oxa-tetramethylene)benzimidazole-N oxide

A mixture of 20.0 g. (72 mmoles) of 4-(2-nitro-4-trifluoromethylphenyl)morpholine and 110 ml. of 20.2% hydrochloric acid was heated at reflux for 20 hours. The resultant solution was cooled to room temperature and extracted twice with 50 ml. of chloroform. The aqueous phase was then evaporated under reduced pressure until nearly dry and the residue dissolved in 50 ml. of water. The aqueous solution was made basic by addition of sodium bicarbonate, precipitating the product as yellow-white crystals. After recrystallization twice from methanol-ether, 2.2 g. of the desired product was obtained as the monohydrate, m.p. 146°–148° C. (decomp.).

EXAMPLE 3

4-(4-tert-butyl-2-nitrophenyl)morpholine 4-tert-Butyl-2-nitrochlorobenzene (19 g.; 68 mmoles) and morpholine (30 g.; 340 mmoles) were heated at 90° C. for 40 hours. The mixture was then poured into ice water. The yellow solid precipitate was collected by filtration (95% yield) and found to melt at 58°–60° C.

EXAMPLE 4

5-tert-Butyl-1,2-(gamma-oxa-tetramethylene)benzimidazole N-oxide

A mixture of 12.0 grams of 4-(4-tert-butyl-2-nitrophenyl) morpholine and 100 ml. of 20% HCl was heated at reflux (110° C.) for 28 hours. The cooled reaction mixture was extracted with 100ml. of methylene chloride to remove unreacted starting material. The aqueous phase was then evaporated under reduced pressure to near dryness and 25 ml. of water added to the residue. After filtration to remove insoluble material, the aqueous solution was neutralized with sodium carbonate. The neutralized solution was extracted thrice with 50 ml. of methylene chloride, the combined extracts dried over anhydrous sodium sulfate and then evaporated under reduced pressure to dryness. The residue was recrystallized from n-hexane and chloroform (10:1) to give 0.35 g. of the desired product, m.p. 109°–114° C. (decomp.). After further recrystallization, the product melts at 136°–138° C. (decomp.).

As described above, the compounds of this invention are useful as intermediates for preparing herbicidal tricyclic morpholinobenzimidazole compounds. The following example illustrates such a preparation.

EXAMPLE 5

5-Trifluoromethyl-1,2-(gamma-oxa-tetramethylene)-benzimidazole

5-Trifluoromethyl-1,2-(gamma-oxa-tetramethylene)-benzimidazole N-oxide (1.1 gram) was hydrogenated in methanol over 0.5 gram of platinum oxide (85%) catalyst. Evaporation of the solvent gave a residue which was extracted with chloroform. The chloroform-soluble material was found to be the desired product (0.97 gram; 88% yield), melting at 129°–131° C.

Use of the 1,2-morpholinobenzimidazoles as herbicides is described and claimed in our copending application Ser. No. 671,452 filed Mar. 29, 1976, now U.S. Pat. No. 4,049,422.

In addition to being useful as intermediates for preparing herbicides, the compounds of this invention have herbicidal activity. They can be applied as either a pre-emergence or a post-emergence treatment; that is, they can be applied to soil in which the plants will grow to kill or suppress the emergence of seedlings of undesirable plants or they can be applied to the foliage of the growing plants after emergence from the soil. Thus, the compounds can be used to control the growth of weeds by applying a phytotoxic amount of one or more of the active compounds of this invention to the locus to be protected; that is, soil in which the weeds are growing or will grow or the foliage of the growing plants. When used as a pre-emergence treatment, the compounds may be applied to the soil surface prior to emergence of the weeds or may be incorporated, such as by mixing into the top 1 to 3 inches (about 2.5 to 7.5 cm.) of the soil prior to planting the crop. When used as a post-emergence treatment, it is preferred that a directed spray be employed, thereby directing the application of the herbicide unto the foliage of the weeds and away from the foliage of the crop plants. Weeds, as used herein, is meant to include any plant growth which is undesirable.

The compounds are especially useful for the post-emergence selective control of weeds such as cocklebur, Jimson-weed, mustard, and velvetleaf in the presence of desirable crops.

Generally, an application rate of from about 0.5 to about 15 pounds (about 0.2 to 7 kg.) of one or more of the active compounds per acre is effective in controlling weed growth. Preferably, an application rate in the range of about 1 to 5 pounds (about 0.4 to 2.3 kg.) per acre is employed.

The following examples illustrate the herbicidal activity of representative compounds of this invention.

EXAMPLE 6

The compounds to be tested were evaluated as both a pre-emergence and post-emergence treatment. Greenhouse flats were planted to soybeans (SB), velvetleaf (VL), oats (O) and millet (M). The flats were sprayed on the same day as planting with an ethanol solution of the compound to be tested at a rate of 5 pounds (2.3 kg.) per acre (Example 2) and 3.3 pounds (1.5 kg.) per acre (Example 4). Another set of flats with the same plants was treated at the same rates after the plants had emerged and were about one inch in height. The flats were kept in the greenhouse and watered when needed. Twenty-one days after treatmet, the flats were examined and the plants rated for herbicidal activity on a 0–9 scale in which 0 = no effect, 1 = <10% injury, 2 = 10–40% injury, 3 = 40–70% injury, 4 = > 70% injury, 5 = < 25% kill, 6 = 25–50% kill, 7 = 50–75% kill, 8 = 75–99% kill and 9 = complete kill. Results are shown in Table I.

TABLE 1

| Compound | Pre | | | | Post | | | |
|---|---|---|---|---|---|---|---|---|
| (Ex.) | SB | VL | O | M | SB | VL | O | M |
| 2 | 3 | 9 | 8 | 7 | 4 | 9 | 9 | 8 |
| 4 | 2 | 9 | 1 | 5 | 6 | 9 | 1 | 9 |

Since a relatively small amount of one or more of the active compounds should be uniformly distributed over the area to be treated, they preferably are formulated with conventional herbicide carriers, either liquid or solid. Thus, the compounds can be impregnated on or admixed with a pulverulent solid carrier such as lime, talc, clay, Bentonite, calcium chloride, vermiculite and the like. Alternatively, they can be dissolved or suspended in a liquid carrier such as water, kerosene, alcohols, diesel oil, mineral oil, xylene, benzene, glycols, ketones, and the like. Since the compounds will form water-soluble salts such as with mineral acids, they can be formulated with water.

A surfactant is preferably included to aid in dispersion, emulsification and coverage. The surfactant can be ionic or non-ionic and may be liquid or solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of naphthalenesulfonic acid, alkylaryl polyether alcohols, long chain quaternary ammonium compounds, sodium salts of petroleum-derived alkylsulfonic acids, polyoxyethylene-sorbitan monolaurate, and the like. These dispersng and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier preferably water, thereby keeping shipping costs to a minimum while providing a product which can be used with a minimum of equipment and effort. Such concentrates may contain from about 5 to about 95 percent by weight of one or more of the active compounds with a carrier or diluent, which may be a liquid or a solid. Liquid carriers which are miscible with the active agent or other liquids in which the compound may be suspended or dispersed, can be used. A surfactant is also generally included to facilitate such dilution or dispersion in water. However, the surfactant itself may comprise the carrier in such concentrates.

Various changes and modifications of the invention can be made, and, to the extent that such variations incorporate the spirit of this invention, they are intended to be included within the scope of the appended claims.

What is claimed is:

1. A compound of the formula

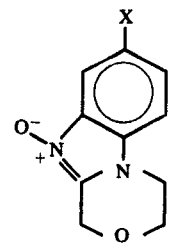

wherein X is a branched-chain alkyl group of 3 to about 6 carbon atoms or trifluoromethyl.

2. A compound according to claim 1 in which X is trifluoromethyl.

3. A compound according to claim 1 in which X is isopropyl.

4. A compound according to claim 1 in which X is tert-butyl.

5. The compound according to claim 1, 5-trifluoromethyl-1,2-(gamma-oxa-tetramethylene)benzimidazole N-oxide.

6. The compound according to claim 1, 5-tert-butyl-1,2-(gamma-oxa-tetramethylene)benzimidazole N-oxide.

7. A herbicidal composition comprising a compound according to claim 1, a surfactant and an inert carrier therefor.

8. The method of controlling undesirable plant growth which comprises applying a phytotoxic amount of a compound according to claim 1 to the locus of said plants.

9. The method according to claim 8 in which said compound is applied to the foliage of said plants.

10. The method according to claim 8 in which said compound is applied at a rate of about 1 to 5 pounds per acre.

11. The method according to claim 8 in wich said X is tert-butyl.

12. The method according to claim 8 in which said X is trifluoromethyl.

* * * * *